(12) United States Patent
Tompkins et al.

(10) Patent No.: US 6,497,713 B1
(45) Date of Patent: Dec. 24, 2002

(54) ROTARY TISSUE CUTTING DIE

(75) Inventors: David Tompkins, Walton-on-Thames (GB); Ernest Lane, Huntington Beach, CA (US); David Hemsley, Rickmansworth (GB)

(73) Assignee: Autogenics, Portola Valley, CA (US)

( * ) Notice: Subject to any disclaimer, the term of this patent is extended or adjusted under 35 U.S.C. 154(b) by 0 days.

(21) Appl. No.: 09/561,119

(22) Filed: Apr. 28, 2000

(51) Int. Cl.[7] .............................................. A61B 17/32
(52) U.S. Cl. ...................................................... 606/167
(58) Field of Search ........................... 606/1, 131, 132, 606/166, 167, 172, 180; 30/301, 316, 358; 623/2; 83/531; 600/564–568

(56) References Cited

U.S. PATENT DOCUMENTS 5,163,955 A    11/1992   Love et al.
5,326,371 A    7/1994    Love et al.
5,425,741 A    6/1995    Lemp et al.
5,609,600 A    3/1997    Love et al.

*Primary Examiner*—David O. Reip
(74) *Attorney, Agent, or Firm*—Knobbe, Martens, Olson & Bear LLP

(57) ABSTRACT

The present invention provides a tissue cutting device and a method for accurately cutting tissue into tissue leaflets for autologous tissue heart valves in a minimal amount of time. The device includes a flexible backing pad located between a rotatable rotary table and a puck which houses several sharpened blades. The tissue to be cut is located on the flexible backing pad adjacent to the blades. The rotary table includes a hemispherically shaped raised cutting bar on the upper surface. When the rotary table is rotated, the cutting bar pushes the tissue against the blades in the puck, cutting the tissue into the desired shape.

18 Claims, 3 Drawing Sheets

ROTARY TISSUE CUTTING DIE

BACKGROUND OF THE INVENTION

1. Field of the Invention

This invention relates to a cutting device, in particular to tissue cutting dies for cutting tissues to a particular configuration, especially for the fabrication of tissue leaflets for preparation of an autologous heart valve.

2. Description of the Related Art

Several types of heart valves are presently available for use in replacing diseased or malfunctioning heart valves in humans.

One form of heart valve is constructed from animal tissue, typically from bovine or porcine aortic valve tissue. The valves constructed from animal tissue typically have short lifetimes. The short lifetimes are caused by two factors. First, there is an antigenic reaction by the body to the animal tissue which causes the tissue to calcify, making it inflexible and more susceptible to failure with time. Second, the tissue is often stored in glutaraldehyde before implantation to try to decrease the antigenic reaction. The aldehyde tends to tan the tissue to a leather-like consistency, which makes the tissue wear out from the repeated stress of opening and closing.

Thus, although heart valves containing animal tissue are widely used, most have to be replaced after about five to ten years. Replacing these valves poses risks to the patient, because a second open heart operation is required, with the attendant possibility of problems during the operation.

Mechanical heart valves are also available. The mechanical valves are made of hard, non-biological materials such as metals or ceramics. Although the mechanical heart valves are durable, the hard, non-biological surfaces on the valves tend to cause blood clots. The blood clots can cause heart attacks or strokes, and, as a result, patients with mechanical heart valves must take anticoagulant drugs. These drugs can lead to hemorrhagic complications.

Another type of heart valve, the autologous tissue valve, is constructed with the patient's own tissue, minimizing the chances of the patient's body rejecting the implanted tissue. A number of patents for autologous tissue heart valves and methods of making autologous tissue heart valves have issued to Autogenics, assignee of this application, including U.S. Pat. Nos. 5,163,955, 5,326,371, and pending U.S. application Ser. No. 09/161,809.

If the patient's own tissue is used to construct the heart valve, the valve must usually be assembled in the same surgical procedure in which the patient's damaged or diseased valve is removed. The valve assembly must be completed quickly to minimize the risk to the patient.

When constructing an autologous heart valve, the patient's tissue is typically mounted on a stent or other type of frame. In one conventional method, valve leaflets are cut from a piece of tissue and are sewn or attached to the frame. In another method, a single piece of tissue is attached to the frame, and the excess tissue is removed. Both methods are time-consuming, causing risk to the patient. In order to reduce the time required to shape the tissue into a form which can be attached to the frame more quickly, tissue cutting dies have been designed.

Two forms of tissue cutting dies are described in the '955 patent. In both forms of the dies, the tissue is cut into the desired shape by pressing a die with embedded blades against a piece of tissue, cutting the tissue in a manner similar to a cookie cutter. Another tissue cutting die is described in U.S. Pat. No. 5,425,741. An actuator with a raised ridge is drawn through a slot in the die. The raised ridge forces the tissue against the blade. A tissue cutting die with a rotatable cutting pad was described in U.S. Pat. No. 5,609,600.

SUMMARY OF THE INVENTION

The present invention provides an improved apparatus and method for cutting a piece of tissue into tissue leaflets for use in autologous tissue heart valves. A significant factor of the invention is that the tissue cutting die is a rotary tissue cutting die that requires less force to operate than previous tissue cutting dies.

The rotary tissue die includes a flexible backing pad for holding the tissue, a housing containing a plurality of blades with a sharpened edge, and a rotary table with a raised cutting bar on the top surface. The cutting bar forces the flexible backing pad against the sharpened edge of the plurality of blades in the housing when the rotary table is rotated, so that the tissue between the flexible backing pad and the housing is automatically cut through.

The flexible backing pad, the housing containing a plurality of blades, and the rotary table are contained in a generally cylindrical body with an end cap. A shaft on the rotary table is connected to a handle. The flexible backing pad is preferably made of polytetrafluoroethylene. Advantageously, the rotary table is made of stainless steel, and the housing containing the plurality of blades is made of polycarbonate.

The blades, the blade housing, and the backing pad are disposable. The cylindrical body and the end cap can be sterilized and reused.

The tissue cutting die of the present invention is used in the following manner. First, a roughly sized piece of tissue is placed on the surface of the flexible backing pad. The plurality of blades with a razor sharpened edge housed in the housing are placed into contact with the tissue. The end cap and the cylindrical body are aligned and secured together. When the handle is turned to rotate the rotary table, the raised cutting bar forces the flexible backing pad against the razor sharpened edge of the plurality of blades in the housing, so that the tissue between the flexible backing pad and the housing is automatically cut through.

DETAILED DESCRIPTION OF THE PREFERRED EMBODIMENT

The present invention describes a rotary tissue cutting die and a method for precisely and accurately cutting tissue to a predetermined configuration. Although described in the context of cutting tissue into tissue leaflets for use in a medical prosthetic device such as an autologous heart valve, it is to be understood that the rotary cutting die may be used for a wide variety of applications, and the application for cutting tissue for a heart valve is not meant to limit the scope of the invention.

The rotary tissue cutting die of the present invention provides several improvements over the cutting dies previously described. First, the rotary tissue cutting die of the present invention provides a robust device which is easy to use due to its simple opening and closing mechanism. Second, the rotary tissue cutting die of the present invention provides a device with improved cutting performance through the application of a single cutting point against the blade. Third, the rotary cutting die is a device where the rotary action requires less force to operate than previous devices. Fourth, the rotary cutting die is a device which is ergonomic to hold and use. Fifth, the rotary cutting die provides a device with a disposable cutter housed within a non-disposable resterilizable actuator body. The inexpensive cutting blades may thus be disposed, while the more expensive actuator body may be reused after sterilization.

Figure 1:
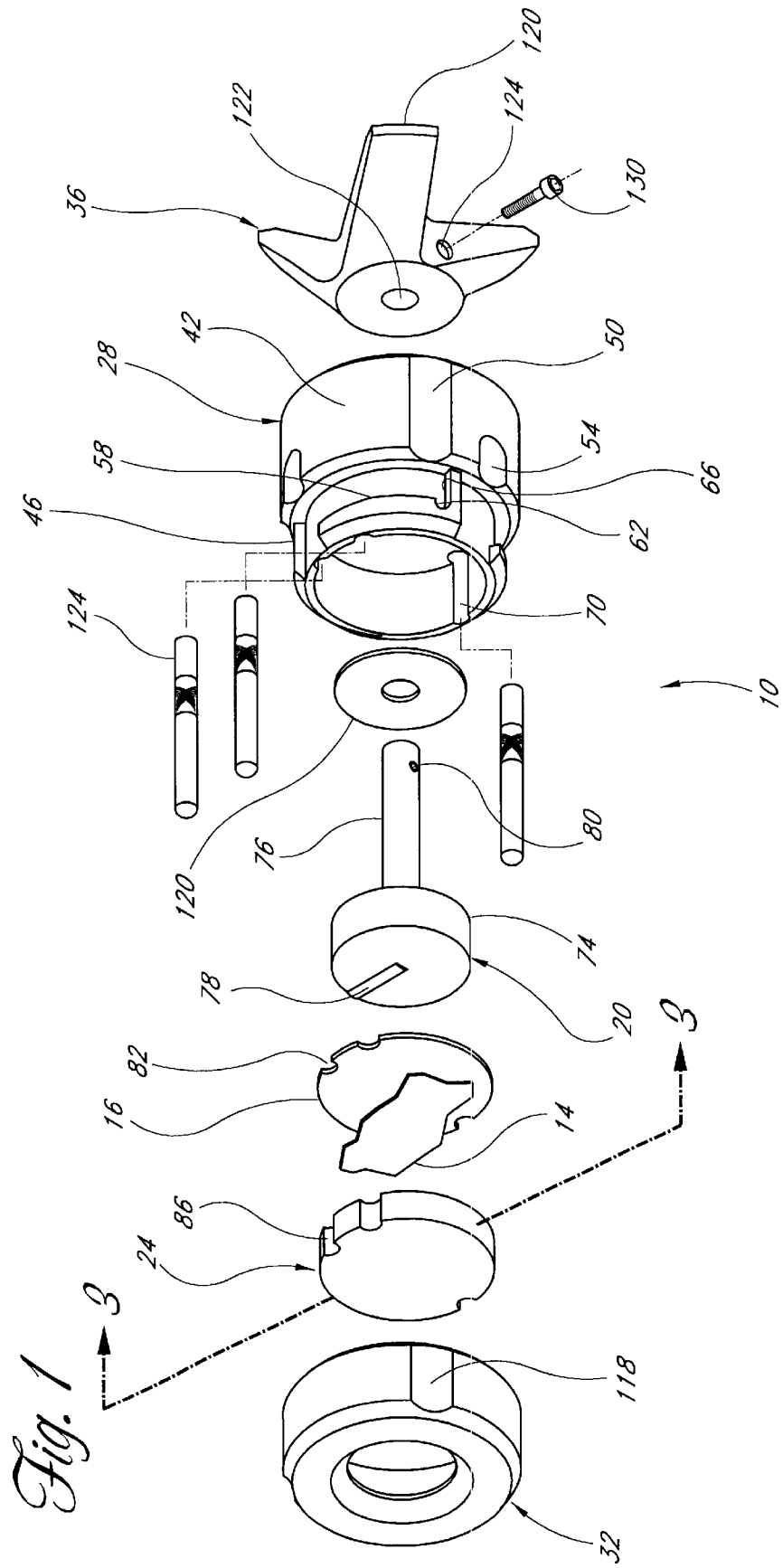
FIG. 1 is a exploded perspective view of an embodiment of a tissue cutting die constructed in accordance with this invention.

FIG. 1 shows an exploded view of a rotary tissue cutting die 10 in accordance with an embodiment of the present invention. As discussed in detail below, an uncut tissue 14 is placed on the surface of a flexible backing pad 16, as shown in FIG. 1. The backing pad 16 and the tissue 14 are placed between a rotary table 20 and a puck 24 containing cutting blades (shown in FIGS. 2A and 2B). The puck 24, the tissue 14 on the backing pad 16, and the rotary table 20 are inserted into an actuator body 28 with the cutting blades on the puck 24 facing the tissue 14. The puck 24, the tissue on the backing pad 16, and the rotary table 20 are secured in the actuator body 28 between an end cap 32 at a first end and a tricorn handle 36 at a second end. When the tricorn handle 36 is turned, the rotary table 20 rotates, pressing the tissue 14 against the cutting blades in the puck 24, cutting the tissue 14 into the desired shape.

Referring to FIG. 1 in more detail, the actuator body 28 has a generally cylindrical shape comprising a cylindrical body portion 42 and a grooved body portion 46, where the cylindrical body portion 42 has a larger outside diameter than the grooved body portion 46. The cylindrical body portion 42 includes a plurality of actuator body long grooves 50 and a plurality of actuator body short grooves 54 on the outer surface. In the embodiment shown in FIG. 1, there are three actuator body long grooves 50 and three actuator body short grooves 54. In other embodiments, there may be more or less actuator body long grooves 50 or actuator body short grooves 54.

Although the actuator body long grooves 50 and the actuator body short grooves 54 provide convenient guides for alignment of the various parts of the rotary tissue cutting die 10, the actuator body long grooves 50 and the actuator body short grooves 54 are not important to the function of the rotary tissue cutting die 10. In some embodiments, the actuator body long grooves 50 and the actuator body short grooves 54 are omitted from the actuator body 28.

The grooved body portion 46 of the actuator body 28 comprises a plurality of ramps 58 on the outer surface of the grooved body portion 46 with a locking notch 62 and a stopping ridge 66 at the end of each of the ramps 58. There are also a plurality of semicircular actuator body cutouts 70 on the inside surface of the grooved body portion 46 of the actuator body 28. In the embodiment shown in FIG. 1, there are three actuator body cutouts 70. In other embodiments, there may be more or less semicircular actuator body cutouts 70.

The rotary table 20 has a "T" shape when viewed from the side, comprising a round table 74 having the shape of a disk and a shaft 76 attached to the bottom of the round table 74. Advantageously, the round table 74 has a smaller diameter than the puck 24 and the backing pad 16. A cutting bar 78 extends approximately halfway across the top of the round table 74. The cutting bar 78 is a raised portion of the round table 74. Advantageously, the cutting bar 78 is hemispherically shaped in cross section. The height of the cutting bar 78 is greater than or equal to the thickness of the tissue 14. Advantageously, the cutting bar 78 is raised approximately 0.040 inches above the surface of the round table 74. A shaft threaded hole 80 is located on the shaft 76 close to an end of the shaft 76 which is not attached to the round table 74. Although in some embodiments the round table 74, the shaft 76, and the cutting bar 78 are separate pieces, in a preferred embodiment, the round table 74, the shaft 76, and the cutting bar 78 which comprise the rotary table 20 are a single piece. The rotary table 20 may be made of a variety of materials including metal or plastic. Stainless steel is an exemplary material of construction for forming the rotary table 20.

The backing pad 16 which holds the tissue 14 has the general shape of a disk, with a plurality of semicircular backing pad cutouts 82 on the edge of the backing pad 16. Although the number of backing pad cutouts 82 can vary, in general the number and locations of the backing pad cutouts 82 are the same as the number and location of the actuator body cutouts 70. In the embodiment shown in FIG. 1, there are three backing pad cutouts 82 and three actuator body cutouts 70. Although the backing pad 16 may be made from a variety of materials, polytetrafluoroethylene, sold by duPont under the trademark of TEFLON™, is an exemplary material for forming the backing pad 16. TEFLON™ is the preferred material for the backing pad 16, because TEFLON™ has a smooth surface with a low coefficient of friction and allows easy penetration of the cutting edges. Although the embodiment of the backing pad 16 shown in FIG. 1 has the general shape of a disk, other shapes of backing pad 14 are also suitable. For example, a square shape or a rectangular shape is also suitable for forming the backing pad 16. The generally disk shaped backing pad 16 as shown in FIG. 1 is a preferred shape for the backing pad 16.

The thickness of the backing pad 16 is chosen so that the backing pad 16 is flexible and can deform in use such that the cutting bar 78 deforms the backing pad 16 when the rotary table 20 is rotated, thereby pushing the tissue 14 against the blades in the puck 24. The backing pad 16 is typically approximately 0.050 inches to 0.080 inches inches thick. In an exemplary embodiment, the backing pad 16 is approximately 0.062 inches thick or less.

The puck 24 has the general shape of a disk with approximately the same diameter as the backing pad 16. There are a plurality of semicircular puck cutouts 86 on the edge of the puck 24. Although the number of puck cutouts 86 may vary, the number and location of the puck cutouts 86 generally correspond to the number and location of the actuator body cutouts 70 and the backing pad cutouts 82.

Figure 2:
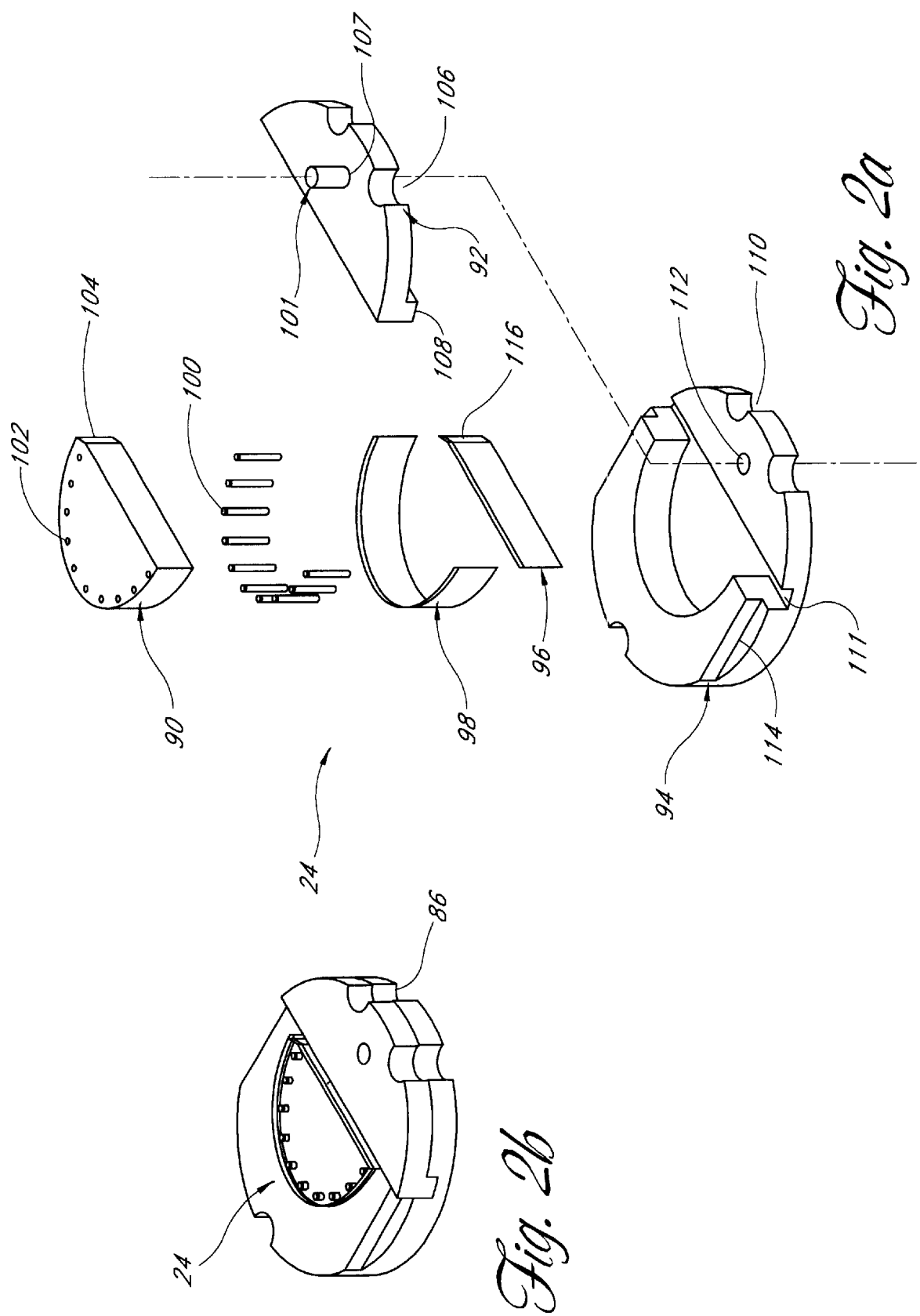
FIG. 2A is an exploded perspective view of an embodiment of the puck portion of the tissue cutting die of FIG. 1.
FIG. 2B is a perspective view of the assembled puck of FIG. 2A.

FIGS. 2A and 2B show the puck 24 in more detail. FIG. 2A shows a perspective exploded view of the puck 24. The puck 24 comprises an island or insert 90, a retainer 92, a puck body 94, a straight blade 96, a curved blade 98, a plurality of circular blades 100, and a puck dowel 101.

The island or insert 90 has a generally semicircular shape with a plurality of round island holes 102 to accommodate the circular blades 100. Although the number of island holes 102 and circular blades 100 vary, depending on the size of the tissue leaflet to be cut, there are 10 island holes 102 and 10 circular blades 100 in the embodiment of the puck 24 of FIG. 2A. In the embodiment shown in FIG. 2A, one edge of the semicircular island or insert 90 has a beveled edge 104, or chamfer. Although not essential, the beveled edge 104 on the island or insert 90 is a preferred embodiment. The island or insert 90 has a shape corresponding to the spatial configuration into which the tissue will be cut.

The retainer 92 has a generally semicircular shape, with a plurality of semicircular retainer cutouts 106 and a round retainer hole 107. There are two semicircular retainer cutouts 106 in the embodiment of the retainer 92 shown in FIG. 2A. A flat side of the retainer 92 comprises a retainer ridge 108 extending downward from the retainer 92 along at least a portion of the flat side of the retainer 92. Although the retainer ridge 108 is not an essential feature of the retainer 92, it is generally preferred that the retainer 92 comprise a retainer ridge 108.

The puck body 94 has the general shape of a disk with a plurality of semicircular shaped puck body cutouts 110. Although the number of puck body cutouts 110 may vary, there are three puck body cutouts 110 in the embodiment of the puck body 94 shown in FIG. 2A. The number and location of the puck body cutouts 110 generally correspond to the number and location of the actuator body cutouts 70 and backing pad cutouts 82. The location of two of the puck body cutouts 110 also correspond with the location of the two retainer cutouts 106. The puck body 94 has a roughly semicircular shaped depression to accommodate the island or insert 90 and a puck body groove 111 to accommodate the retainer ridge 108 on the retainer 92. The puck body 94 also includes a round puck body hole 112 to accommodate the puck dowel 101. In the embodiment shown in FIG. 2A, the puck body 94 also includes two shoulders 114 cut into the puck body 94 to allow entry of a lever to assist in the removal of the backing pad after the cutting operation. Although the island or insert 90, the retainer 92, and the puck body 94 may be made from a variety of materials including metals or plastics, in an exemplary embodiment, the island or insert 90, the retainer 92, and the puck body 94 are formed from polycarbonate. Suitable forms of polycarbonate are available from General Electric under the trade name of LEXAN™ or from Mobay under the trade name of MERLON™, though other forms of polycarbonate are also suitable.

Although the embodiment of the puck 24 shown in FIGS. 2A and 2B has blades in the shape of the straight blade 96, the curved blade 98, and the circular blades 100, it is to be understood that the blades may be of any shape, and the blades to be used with the rotary tissue die 10 of the present invention are not limited to the embodiments shown in FIGS. 2A and 2B.

The straight blade 96 shown in FIG. 2A has a bend 116 which corresponds to the shape and location of the beveled edge 104 or chamfer on the retainer 90. In other embodiments, the straight blade 96 does not have the bend 116. It is generally preferred that the straight blade 96 comprise the bend 116, so that the tissue leaflets which are prepared from the tissue 14 with the rotary cutting die 10 will have a chamfer on one edge.

The straight blade 96, the curved blade 98, and the circular blades 100 are advantageously formed from thin case hardened corrosion resistant material such as stainless steel having sufficient flexibility to conform to the shape of the gap between the island or insert 90 and the puck body 94 or the gap between the retainer 92 and the puck body 94. The blade thickness should, however, be sufficient to prevent deflection of the blade, and consequently, an inadequately cut piece of tissue. In an exemplary embodiment, the straight blade 96, the curved blade 98, and the circular blades 100 are made from a strip of approximately 0.006 inch thick stainless steel having a razor-sharpened edge. One suitable supplier of blades is American Safety Razor of West Virginia. Other blades having similar properties are suitable for use in the present invention.

The puck 24 is assembled in the following fashion. The circular blades 100 are placed into the island holes 102 on the island or insert 90, where they are held in place by friction with the walls of the island holes 102. The curved blade 98 is placed in the semicircular shaped depression in the puck body 94, and the island or insert 90 is placed next to the curved blade 98. The straight blade 96 is placed on the straight side of the island or insert 90 with the bend 116 of the straight blade 96 adjacent to the beveled edge 104 or chamfer on the island or insert 90. The straight blade 96 is held against the island or insert 90 by inserting the retainer ridge 108 on the retainer 92 into the slot 111 of the puck body 94. The retainer 92 is held in position in the puck body 94 by inserting the retainer dowel 101 into the retainer hole 107 on the retainer 92 and the puck body hole 112 on the puck body 94. The assembled puck 24 is shown in FIG. 2B.

The straight blade 96 fits into the gap between the island or insert 90 and the retainer 92. The curved blade 98 fits into the gap between the puck body 94 and the island or insert 90. The gaps are small enough that the straight blade 96 and the curved blade 98 are held firmly in place. All of the blades 96, 98, and 100 are placed into the puck 94 so that the sharpened edges of the blades are exposed on the top of the puck 94.

The dimensions of the blades 96, 98, and 100, the puck body 94, the insert 90, and the retainer 92 are such that the blades protrude above the surface of the puck 24 by approximately 0.035 inches or 35 mil, slightly more than the thickness of the tissue being cut.

Returning to FIG. 1, the end cap 32 fits over the assembled puck 24. The end cap 32 has an annular shape with a plurality of end cap short grooves 118 on the outside of the end cap 32. The end cap short grooves 118 are for convenience in aligning the end cap 32 with the actuator body 28 and are not essential for the operation of the rotary tissue cutting die 10. In some embodiments, there are no end cap short grooves 118 on the end cap 32. There are two pegs or posts (not shown) on the inside of the end cap 32.

Although the end cap 32 may be manufactured of a variety of materials such as metal or plastic, polycarbonate is a preferred material for forming the end cap 32. Suitable forms of polycarbonate are available from General Electric under the trade name of LEXAN™ or from Mobay under the trade name MERLON™. Other forms of polycarbonate are also suitable for forming the end cap 32.

The tricorn handle 36 has an annular shape with a plurality of handles 120 extending outward from the annulus. The embodiment of the tricorn handle 36 shown in FIG. 1 has three handles 120. Other embodiments of the tricorn handle 36 can have different numbers of handles 120. In an alternative embodiment, there are no handles 120 on the tricorn handle 36. There is a shaft hole 122 in the center of the tricorn handle 36 and a threaded hole 124 on the side of the tricorn handle 36. Although it is generally preferred that there are a plurality of threads on the inside of the threaded hole 124, in some embodiments there are no threads on the inside of the threaded hole 124. The tricorn handle 36 can be made of a variety of materials, including metal or a wide range of plastics. In an exemplary embodiment, the tricorn handle 36 is made of polycarbonate. Suitable forms of polycarbonate are available from General Electric under the trade name of LEXAN™ or from Mobay under the trade name of MERLON™. Other forms of polycarbonate are also suitable for forming the tricorn handle 36.

A annular shaped thrust washer 120 is located between the rotary table 20 and the actuator body 28. The thrust washer 120 reduces the friction between the rotary table 20 and the actuator body 28.

The tissue cutting die 10 is assembled as follows. The shaft 76 on the rotary table 20 is inserted into the annular shaped thrust washer 120, and the rotary table 20 and the thrust washer 120 are inserted into the actuator body 28. The backing pad 16 with the uncut tissue 14 is placed on the rotary table 20 with the tissue 14 on the side of the backing pad 16 opposite the side of the backing pad 16 which faces the rotary table 20. The assembled puck 24 is placed over the backing pad 16 and the uncut tissue 14, with the sharpened edges of the blades 96, 98, and 100 in the puck 24 contacting the tissue 14. A. plurality of dowels 124 are inserted into the actuator body cutouts 70, the backing pad cutouts 82, and the puck cutouts 86, so that the backing pad 16 and the puck 42 do not rotate when the rotary table 20 rotates. In an exemplary embodiment, the diameter of the rotary table 20 is smaller than the diameters of the backing pad 16 and the puck 42, so that the rotary table 20 can be rotated without contacting the dowels 124 which hold the backing pad 16 and the puck 24 in place.

The shaft hole 122 on the tricorn handle 36 is placed onto the shaft 76 of the rotary table 20, and a fixing 130 is inserted into the threaded hole 124 on the tricorn handle 36 and the shaft threaded hole 80 on the shaft 76 of the rotary table 20, so that the tricorn handle 36 is rigidly attached to the shaft 76 of the rotary table 20. In the embodiment shown in FIG. 1, the fixing 130 is a screw, and both the threaded hole 124 on the tricorn handle 36 and the shaft threaded hole 80 on the rotary table 20 have threads on the inside of the holes. In other embodiments, the fixing 130, the shaft threaded hole 80, and the threaded hole 124 on the tricorn handle 36 are not threaded, and the fixing 130 is held in place by friction.

The end cap 32 is placed over the puck 24 and the actuator body 28 with the end cap short grooves 118 aligned with the actuator body short grooves 54. The end cap 32 is then turned one-quarter turn clockwise so that the end cap short grooves 118 are aligned with the actuator body long grooves 50. The pegs (not shown) on the inside of the end cap 32 engage the ramps 58 on the outside surface of the grooved body portion 46 of the actuator body 28. When the end cap 32 is rotated, the pegs on the inside of the end cap 32 tighten the end cap 32 onto the actuator body 28. After the pegs contact the stopping ridge 66 at the end of the ramp 58 on the actuator body 28, the pegs engage the locking notch 62 on the outside of the grooved body portion 46 of the actuator body 28 to lock the end cap 32 and the puck 24 into position on the actuator body 28.

Cutting the Tissue

The autologous pericardial tissue is initially cleaned in situ, harvested and partially fixed in glutaraldehyde. The cleaning, harvesting, and fixing processes for the autologous tissue are known in the art and are described, for example, in U.S. Pat. No. 5,163,955, herein incorporated by reference. The tissue 14 is cut with a scalpel to fit the rotary tissue cutting die 10. The tissue 14 is placed on the backing pad 16, the puck 24 is placed onto the backing pad 16 with the blades 96, 98, and 100 contacting the tissue 14, the end cap 32 is placed over the backing pad 16 and the puck 24, and the end cap 32 is tightened onto the actuator body 28. In order to cut the tissue 14 into a tissue leaflet, the tricorn handle 36 is rotated a single turn in either a clockwise or a counterclockwise direction. The cutting bar 78 on the rotary table 20 forces the tissue 14 on the backing pad 16 into contact with the blades 96, 98, and 100 on the puck 24. The cutting bar 78 produces a "wave" in the tissue 14 and the backing pad 16, sequentially pushing portions of the tissue 14 into contact with the blades 96, 98, and 100, enabling the blades to work in shear.

Figure 3:
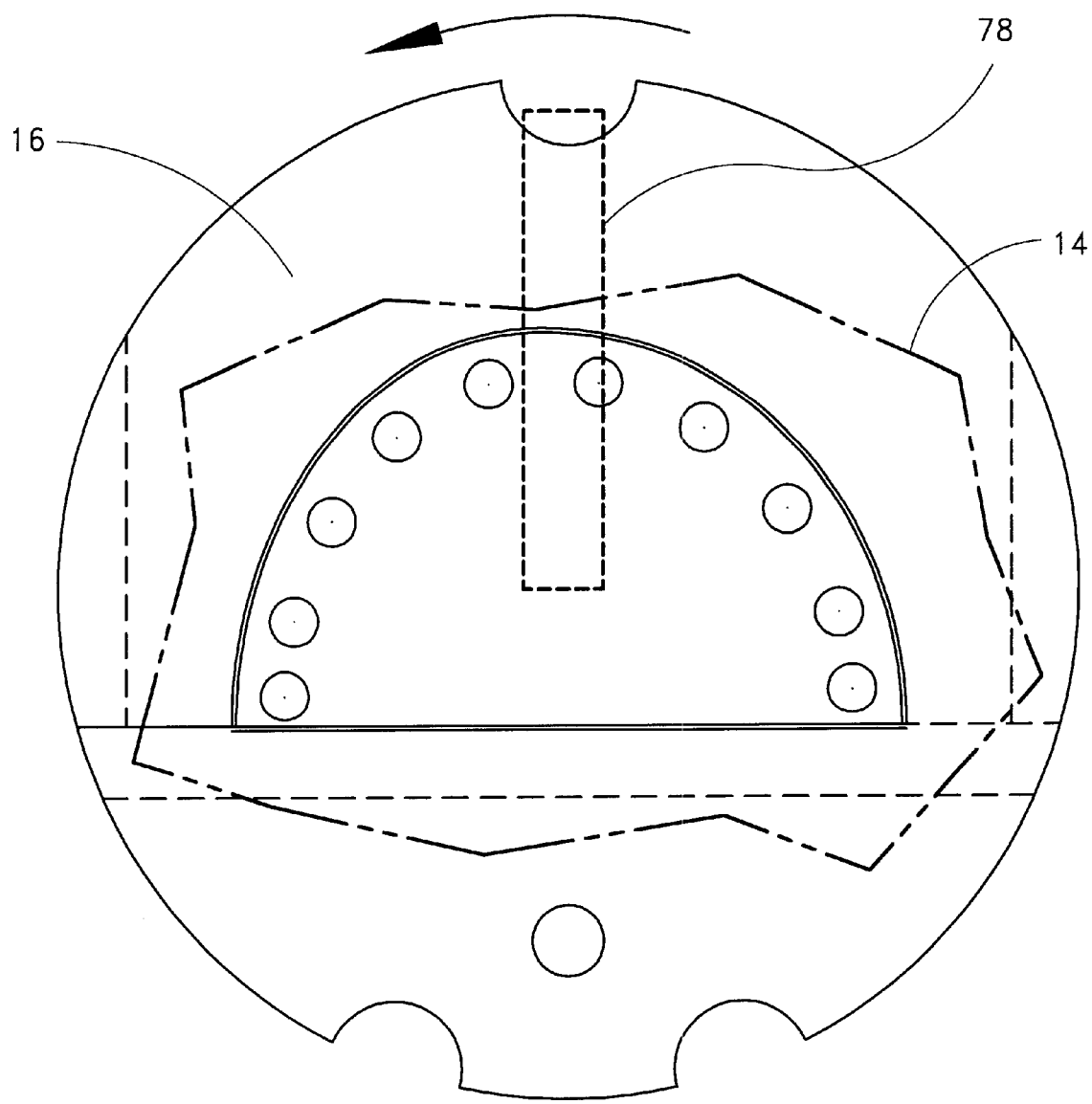
FIG. 3 is a cross-sectional view taken along line 3—3 of FIG. 1, showing how the cutting bar on the rotary table sweeps around the cutting blades in the puck, pressing the tissue against the cutting blades.

FIG. 3 shows an cross sectional view along the 3—3 axis of FIG. 1 showing the tissue 14 on the backing pad 16 with the cutting bar 78 underneath the backing pad 16. The cutting bar 78 is shown in dotted lines, because the cutting bar 78 is located underneath the backing pad 16 and cannot be seen in the view of FIG. 3. The puck 24 with the cutting blades 96, 98, and 100 is located above the tissue 15. As the rotary table 20 under the backing pad 16 is turned, the cutting bar 78 sweeps around the cutting blades 96, 98, and 100, pressing the tissue 14 against the cutting blades 96, 98, and 100.

The cut tissue 14 is removed from the tissue cutting die 10 by rotating the end cap 32 in a counterclockwise direction until the end cap short grooves 118 are aligned with the actuator body short grooves 54. The end cap 32 is lifted off of the actuator body 28. The actuator body 28 is placed onto a flat surface on the tricorn handle 36, and the actuator body 28 is pressed downwards towards the tricorn handle 36. This action raises the backing pad 16, the cut tissue 14, and the puck 24 from the actuator body 28. The puck 24 and the backing pad 16 are lifted off of the actuator body 28 and are placed on a level surface, puck 24 downward. A lever is inserted into the shoulders 114 of the puck body 94 to assist in separating the puck 24 and the backing pad 16. The backing pad 16 is then lifted to expose the cut tissue 14. Forceps are used to lift out the cut tissue 14. The cut tissue 14, for example forming one leaflet of the tricuspid replacement aortic valve, is set aside ready to construct the heart valve. The used puck 24 and the backing pad 16 are safely discarded. The actuator body 28 and the end cap 32 are used to cut further leaflets or are cleaned and resterilized for later use.

As best seen in FIG. 3, the circular blades 100 cut small holes into the tissue leaflet. The tissue leaflets with the small holes can be used in heart valves having at least one stent configured with a plurality of posts, where each of the posts include outwardly-projecting tissue alignment members. The small holes in the tissue leaflet which are cut with the circular blades 100 are configured to fit over the outwardly-projecting tissue alignment members on the stent, holding the tissue leaflet on the stent.

The rotary action of the rotary tissue cutting die 10 requires less force to operate than previous tissue cutting dies. In the described embodiment, the rotary tissue cutting die 10 provides a single leaflet cut precisely to the shape required for the autologous pericardial tissue valve (APHV) 9 shown in FIG. 1. The rotary tissue cutting die 10 can be used to cut autologous, homologous, heterologous, engineered, or synthetic tissue into leaflets for a heart valve. A single actuator body 28 can be used to cut leaflets of various sizes by varying the size of the blades and the other parts which make up the puck 24. The rotary tissue cutting die 10 therefore provides a great deal of flexibility for cutting tissue leaflets for heart valves.

While embodiments and applications of the present invention have been described, it should be understood by those skilled in the art that many more modifications are possible without departing from the scope of the invention. The invention is not meant to be restricted, except in the spirit of the claims.

What is claimed is:

1. An apparatus for cutting a piece of tissue into a tissue leaflet for use in a heart valve, said apparatus comprising:
   a flexible backing pad for holding the piece of tissue
   a blade housed in a housing juxtaposed said flexible member; and
   a rotary table rotatingly mounted proximate to said member, said rotary table including a shaft and a raised cutting bar, wherein said raised bar forces a proximal portion of said flexible member against said blade when said rotary table rotates, so that tissue retained between said flexible member and said blade is automatically cut through when said rotary table rotates.

2. The apparatus of claim 1, further comprising a handle attached to said shaft.

3. The apparatus of claim 1, further comprising a generally cylindrical body containing said flexible member, said blade housed in said housing, and said rotary table.

4. The apparatus of claim 1, wherein said flexible member, said blade housed in said housing, and said housing are disposable.

5. The apparatus of claim 1, wherein said raised cutting bar is linear.

6. The apparatus of claim 1, wherein said flexible member is made of polytetrafluoroethylene.

7. The apparatus of claim 1, wherein said flexible member is approximately 0.062 inches thick or less.

8. The apparatus of claim 1, wherein said rotary table is made of a stainless steel material.

9. The apparatus of claim 1, wherein the housing housing said blade is made of a polycarbonate material.

10. The apparatus of claim 1, wherein said blade is made of a high quality corrosion resistant material with a razor sharpened edge.

11. The apparatus of claim 10, wherein said blade is made of stainless steel.

12. The apparatus of claim 1, wherein said blade is approximately 0.006 inch thick.

13. The apparatus of claim 1, wherein said blade housed in said housing extends approximate 35 mils from said housing.

14. An apparatus for cutting a piece of tissue into a tissue leaflet for use in a heart valve, said apparatus comprising:
   a flexible member holding the piece of tissue;
   a blade housed in a housing juxtaposed said flexible member;
   a rotary table rotatingly mounted proximate to said member, said rotary table including a raised cutting bar, wherein said raised bar forces a proximal portion of said flexible member against said blade when said rotary table rotates, so that tissue retained between said flexible member and said blade is automatically cut through when said rotary table rotates;
   a generally cylindrical body containing said flexible member, said blade housed in said housing and said rotary table; and
   an end cap for retaining said flexible member, said blade housed in said housing, and said rotary table in said generally cylindrical body.

15. The apparatus of claim 14, wherein said end cap and said generally cylindrical body are sterilizable and reusable.

16. An apparatus for cutting a piece of tissue into a tissue leaflet for use in a heart valve, said apparatus comprising:
   a flexible member holding the piece of tissue;
   a blade housed in a housing juxtaposed said flexible member;
   a rotary table rotatingly mounted proximate to said member, said rotary table including a raised cutting bar, wherein said raised bar forces a proximal portion of said flexible member against said blade when said rotary table rotates, so that tissue retained between said flexible member and said blade is automatically cut through when said rotary table rotates; and
   wherein said housing comprises an insert having a shape corresponding to the spatial configuration into which the tissue will be cut, said insert fitting into a depression in said housing.

17. The apparatus of claim 16, wherein fitting said insert into said depression in said housing creates a narrow gap between said insert and said housing.

18. The apparatus of claim 17, wherein said blade is positioned in said narrow gap between said island and said housing.

* * * * *

UNITED STATES PATENT AND TRADEMARK OFFICE
CERTIFICATE OF CORRECTION

PATENT NO.   : 6,497,713 B1
DATED        : December 24, 2002
INVENTOR(S)  : David Tompkins et al.

It is certified that error appears in the above-identified patent and that said Letters Patent is hereby corrected as shown below:

<u>Column 9,</u>
Line 8, "backing pad for" should be -- member --; a semicolon should follow "tissue"

Signed and Sealed this

Twenty-fifth Day of November, 2003

JAMES E. ROGAN
*Director of the United States Patent and Trademark Office*